United States Patent [19]

Lewis et al.

[11] Patent Number: 5,714,055
[45] Date of Patent: Feb. 3, 1998

[54] CAUSTIC TOWER TRAP FOR ACETALDEHYDE

[75] Inventors: Vincent E. Lewis, Missouri City; Natu R. Patel, Houston, both of Tex.

[73] Assignee: Nalco/Exxon Energy Chemicals, L.P., Sugar Land, Tex.

[21] Appl. No.: 695,448

[22] Filed: Aug. 12, 1996

[51] Int. Cl.$^6$ ..................................... C10G 9/12
[52] U.S. Cl. .................. 208/48 R; 208/48 AA; 585/950
[58] Field of Search ............... 208/48 AA, 48 R; 585/950

[56] References Cited

U.S. PATENT DOCUMENTS

| | | | |
|---|---|---|---|
| 3,328,284 | 6/1967 | Godar | 208/48 AA |
| 4,673,489 | 6/1987 | Roling | 208/289 |
| 4,775,458 | 10/1988 | Forester | 208/48 AA |
| 4,952,301 | 8/1990 | Awbrey | 208/48 AA |
| 5,160,425 | 11/1992 | Lewis | 208/95 |
| 5,264,114 | 11/1993 | Dunbar | 208/48 HA |
| 5,288,394 | 2/1994 | Lewis et al. | 208/48 AA |

*Primary Examiner*—Glenn Caldarola
*Assistant Examiner*—Thuan D. Dang
*Attorney, Agent, or Firm*—Robert A. Miller; James J. Drake

[57] ABSTRACT

A method of inhibiting the formation of fouling deposits occurring on the surfaces of an alkaline scrubber used to wash acid gases generated during the manufacture of olefins, which deposits are formed during the scrubbing of pyrolytically produced hydrocarbons contaminated with oxygen-containing compounds with a caustic solution having a pH>7, which comprises adding an effective depositing-inhibiting amount of a caustic solution-soluble substituted aromatic amine selected from the group consisting of: 2-aminophenol, 4-aminophenol, 4-aminobenzenesulfonic acid and salts thereof, 4-amino-o-cresol, 3-aminophenol, 2-aminobenzoic acid and salts thereof, 3-aminobenzoic acid and salts thereof, and 4-aminobenzoic acid and salts thereof to the caustic solution. A preferred substituted aromatic amine is the sodium salt of 4-amino-benzenesulfonic acid in aqueous solution.

14 Claims, No Drawings

CAUSTIC TOWER TRAP FOR ACETALDEHYDE

FIELD OF THE INVENTION

A method of inhibiting the formation of fouling deposits occurring on the surfaces of an alkaline scrubber used to wash acid gases generated during the manufacture of olefins, which deposits are formed during the scrubbing of pyrolytically produced hydrocarbons contaminated with oxygen-containing compounds with a caustic solution having a pH>7, which comprises adding an effective deposit-inhibiting amount of a caustic solution-soluble substituted aromatic amine selected from the group consisting of: 2-aminophenol, 4-aminophenol, 4-aminobenzenesulfonic acid and salts thereof, 4-amino-o-cresol, 3-aminophenol, 2-aminobenzoic acid and salts thereof, 3-aminobenzoic acid and salts thereof, and 4-aminobenzoic acid and salts thereof to the caustic solution. A preferred substituted aromatic amine is the sodium salt of 4-amino-benzenesulfonic acid in aqueous solution.

BACKGROUND OF THE INVENTION

This invention relates to the prevention of fouling on metal surfaces in contact with a sodium hydroxide solution which is in contact with a gaseous or liquid hydrocarbon stream.

In cracking operations, such as the pyrolytic cracking of ethane, propane, and naphtha to form olefins, oxygenated compounds, including carbonyl compounds, are formed. The amount of carbonyl compounds, such as aldehydes and ketones, formed in such operations can vary widely, but is typically about 1-100 ppm in the gas stream with concentrations as high as 1000 ppm occasionally being encountered because of the utilization of various feedstocks and cracking temperatures. When the gas stream is passed through a basic wash (pH>7) to remove acidic components such as hydrogen sulfide and carbon dioxide, oxygen containing compounds, such as carbonyl compounds are also removed. These oxygen containing compounds, particularly acetaldehyde, will undergo polymerization in the presence of the basic wash or scrubbing conditions. In the wash tower, the resulting polymer settles on the trays leading to fouling and eventual plugging of the trays. Eventually the unit must be shut down for cleaning—obviously a costly operation. The basic wash systems, where treatment is required to inhibit such polymer-based fouling, include amine scrubbers (e.g. monoethanolamine (MEA) and diethanolamine (DEA) and caustic (sodium hydroxide) wash systems.

Generally, the basic washing entails contacting the gaseous olefins with an aqueous basic solution in a wash tower to remove hydrogen sulfide and carbon dioxide therefrom. The conditions in the wash tower are conducive for condensation reactions of any aldehydes (e.g. acetaldehyde) and/or ketones contained therein.

Carbohydrazide has been found to be an effective antifoulant for ethylene unit caustic towers and amine units used to scrub gases after the furnace but prior to the recovery section. During ethylene production, a small amount of partial oxidation products are formed. The major component of these partial oxidation products is acetaldehyde. The effluent from the ethylene furnace, containing acetaldehyde and other oxidation products, is washed in a caustic tower. This process removes acid gases such as carbon dioxide and hydrogen sulfide. Carbohydrazide has been disclosed as useful for inhibiting polymeric fouling deposits during the caustic scrubbing of pyrolyticallyproduced hydrocarbons contaminated with oxygen-containing compounds in U.S. Pat. No. 5,160,425.

In some ethylene production units, an amine unit is used in front of the caustic tower to remove most of the acid gases. On contact with a caustic or aqueous amine solution, acetaldehyde and other aldehydes or ketones undergo a base catalyzed Aldol condensation. The result of these numerous Aldol reactions is a water insoluble polymer.

At some ethylene manufacturing facilities, a vinyl acetate plant is also present. Ethylene is used in the vinyl acetate production process. Unreacted ethylene is recovered by distillation and sent back through the ethylene unit fractionization train. Vinyl acetate can be entrained with the unreacted ethylene and enter the fractionization train. When vinyl acetate reaches the caustic tower, it is hydrolyzed to produce a salt of acetic acid and acetaldehyde, a source of the fouling polymer.

In U.S. Pat. No. 4,673,489, hydroxylamine and its hydrochloride and hydrogen sulfate salts have been used to inhibit polymer formation caused by condensation reactions of aldehydes contained in caustic scrubber units. Similarly, hydrazide compounds for inhibiting the formation and deposition of polymer-based fouling materials after caustic scrubbing of hydrocarbon streams are disclosed in U.S. Pat. No. 5,288,394. However, despite the success of such treatments, these compounds are expensive and must be overfed to the caustic scrubber units.

Similarly, in U.S. Pat. No. 4,952,301, ethylenediamines and water soluble salt forms thereof have been used to inhibit carbonyl based fouling, particularly aldehyde fouling, that often occurs during caustic scrubbing of liquid or gas phase hydrocarbon streams. Amino-containing aryl compound have been disclosed as inhibitors for formation and deposition of fouling materials during caustic washing of hydrocarbon gases in U.S. Pat. No. 5,264,114. However, as the Examples show, not all amine-containing aryl compounds are effective for this purpose. Moreover, some are not even soluble under caustic washing conditions because of high pH.

SUMMARY OF THE INVENTION

A method of inhibiting the formation of fouling deposits occurring on the surfaces of an alkaline scrubber used to wash acid gases generated during the manufacture of olefins, which deposits are formed during the scrubbing of pyrolytically produced hydrocarbons contaminated with oxygen-containing compounds, with a caustic solution having a pH>7, which comprises adding an effective deposit-inhibiting amount of a caustic solution-soluble substituted aromatic amine selected from the group consisting of: 2-aminophenol, 4-aminophenol, 4-aminobenzenesulfonic acid and salts thereof, 4-amino-o-cresol, 3-aminophenol, 2-aminobenzoic acid and salts thereof, 3-aminobenzoic acid and salts thereof, and 4-aminobenzoic acid and salts thereof to the caustic solution. A preferred substituted aromatic amine is the sodium salt of 4-amino-benzenesulfonic acid in aqueous solution.

DESCRIPTION OF THE INVENTION

This invention relates to a method of inhibiting formation of fouling deposits during the basic washing of hydrocarbons contaminated with oxygen containing compounds. The method comprises adding to the wash an effective amount of a substituted aromatic amine. The treatment is well suited for inhibition of deposits formed during the caustic scrubbing of gas phase olefinic hydrocarbons resulting from the pyrolytic cracking process. This method prevents the carbonyl compounds, including ketone and aldehyde contaminants, from undergoing Aldol condensation and thereby forming insoluble polymer molecules. By eliminating the formation of insoluble contaminants, system equipment is kept free of fouling deposits.

The invention is a method of inhibiting the formation of fouling deposits occurring on the surfaces of an alkaline scrubber used to wash acid gases generated during the manufacture of olefins, which deposits are formed during the scrubbing of pyrolytically produced hydrocarbons contaminated with oxygen-containing compounds with an alkaline solution having a pH>7, which comprises adding an effective deposit-inhibiting amount of an alkaline solution-soluble substituted aromatic amine selected from the group consisting of: 2-aminophenol, 4-aminophenol, 4-aminobenzenesulfonic acid and salts thereof, 4-amino-o-cresol, 3-aminophenol, 2-aminobenzoic acid and salts thereof, 3-aminobenzoic acid and salts thereof, and 4-aminobenzoic acid and salts thereof to the alkaline solution. In this method, a preferred substituted aromatic amine is the sodium salt of 4-aminobenzenesulfonic acid. The scrubber may be a caustic scrubber or an amine scrubber. An amine unit performs similarly to a caustic unit. In a typical amine unit, the amine (usually 10% diethanolamine in water) circulates between the absorber and stripper. The cracked gas stream enters the absorber and acid gases (carbon dioxide and hydrogen sulfide) react with the amine. This amine salt (called rich amine) is carried out the bottom of the absorber and sent to the stripper. The temperature of the bottoms of the stripper are around 275° F. This is hot enough to cause the amine salts to dissociate; releasing carbon dioxide and hydrogen sulfide which are carded overhead and sent to the flare. The amine without the salts (lean amine) is sent back to the absorber to react with more acid gases. Acetaldehyde reacts with the amine to form an enamine, which would be stable if there was not water present. In the presence of water, the enamine reacts further with acetaldehyde to form polymer just as it does in the caustic tower.

Further, the substituted aromatic amine may be recovered for re-use. The pyrolytically-produced hydrocarbon may be an olefin. Additionally, the hydrocarbons may be produced by the pyrolytic cracking of hydrocarbon feedstocks. The hydrocarbon feedstocks may be selected from the group consisting of ethane, propane, butane, naphtha and mixtures thereof. The hydrocarbon may be in a gaseous phase.

The oxygen-containing compound may be a carbonyl compound. Moreover, the carbonyl compound may be acetaldehyde.

The substituted aromatic amine may be added to the alkaline scrubber in an amount representing a molar ratio of amine to carbonyl from about 1.0:10.0 to about 1.0:25.0. Preferably, the substituted aromatic amine may be added to the alkaline scrubber in an amount representing a molar ratio of amine to carbonyl from about 1.0:3.0 to about 1.0:9.0. Most preferably, the substituted aromatic amine may be added to the alkaline scrubber in an amount representing a molar ratio of amine to carbonyl from about 1.0:1.0 to about 1.0:2.0.

In accordance with the invention, the substituted aromatic amine is added to the aqueous medium of a basic (i.e., pH>7) wash or scrubber system. The fouling inhibitor can be added to the caustic tower as neat material or in solution form. The preferred method of addition is as an aqueous solution with 0.1 to 20 weight percent inhibitor present, with 10 weight percent especially preferred, so that accurate metering of the inhibitor to the tower can be achieved.

The treatment should be added to the wash in sufficient quantity to assure that the molar amount of inhibitor is sufficient to react with all of the undesirable carbonyl contaminants. Treatment ranges of from 1 to 10,000 ppm of inhibitor per one million parts of the aqueous scrubbing medium may be used if no convenient method of measuring carbonyl content is available. Specifically, treatment ranges of from 100 to 200 ppm of inhibitor have been successfully used. In any event, an effective amount of inhibitor should be used to inhibit the formation of fouling deposits during the basic washing of hydrocarbons contaminated with carbonyl compounds.

The treatment is especially well adapted to inhibit fouling in caustic wash systems wherein gaseous olefinic compounds are washed. These gas phase olefins comprise ethylene, propylene, butadiene, etc., which are formed from the pyrolytic cracking of hydrocarbon feedstock such as ethane, propane, butane, naphtha, or mixtures thereof. The invention may be utilized in any alkaline wash system but is particularly useful in caustic washes such as sodium hydroxide, potassium hydroxide, and in some of the organic amine materials. The invention is further illustrated by the following example which is intended merely for the purpose of illustration and is not to be regarded as limiting the scope of invention or the manner in which it may be practiced.

EXAMPLE 1

To a 10 ml aliquot of 10% aqueous sodium hydroxide solution, 0.055 moles of the particular amine to be tested was added to give a clear solution. To this solution 0.5 ml of vinyl acetate (0.055 mole) was added and shaken vigorously to hydrolyze vinyl acetate to acetaldehyde in situ. The solution was set aside overnight and physical characteristics were compared with the blank (containing no aromatic amine). The blank showed red precipitates. The test was also run using acetaldehyde instead of vinyl acetate with the same results.

The results of Table I illustrate that 1,2 amino-phenol effectively prevents precipitation, while another substituted aromatic compound, 1,2, phenylene diamine is not even soluble under pertinent conditions. 1,2 phenylene diamine is not even soluble under pertinent conditions. This shows that not every aromatic amine is suitable for use in caustic or amine units.

TABLE I

Precipitation Test Results

| | Observations | |
|---|---|---|
| Substituted Aryl Amine | at 24 hrs. | at 96 hrs. |
| none | orange ppt | orange ppt |
| 1,2-phenylenediamine | insoluble | insoluble |
| 2-aminophenol | clear red sol'n | clear red sol'n |
| 2-hydroxybenzoic acid | yellow suspension | orange ppt |

EXAMPLE 2

The procedure described in Example 1 was utilized to obtain the results of Table II. Table II illustrates that some aromatic amines can effectively prevent precipitation under pertinent conditions, and that comparable results are produced by a conventional carbohydrazide treatment. This shows that the amino group is necessary for inhibition; but again as shown above, not all aromatic amines are suitable.

TABLE II

Precipitation Test Results

| Amine | Amount (g) | Observations at 24 hrs. | at 96 hrs. |
|---|---|---|---|
| none | none | red ppt | red ppt |
| 2-aminophenol | 0.59 | red sol'n | red sol'n |
| 4-aminobenzenesulfonic acid | 0.95 | amber sol'n | amber sol'n |
| 4-amino-o-cresol | 0.76 | red sol'n | red sol'n |
| 2-methoxyphenol | 0.68 | red ppt | red ppt |
| 3,4,5-trimethoxyphenol | 1.01 | red ppt | red ppt |
| carbohydrazide | 0.505 | clear sol'n | clear sol'n |
| carbohydrazide | 1.01 | clear sol'n | clear sol'n |

EXAMPLE 3

The procedure described in Example 1 was utilized to obtain the results of Table III. These results also illustrate that some aromatic amines are effective to prevent undesirable precipitation.

The substituted aromatic amines of the instant invention, such as 2-aminobenzoic acid, can be recovered for re-use by adding mineral acid dropwise until a pH of 5 is reached. The solution is filtered, and the precipitates are dried. FTIR of the residue confirms the presence of the substituted aromatic amine, 2-amonobenzoic acid.

TABLE III

| Amine | Amount (g) | Observations at 1 hr. | at 48 hrs. |
|---|---|---|---|
| none | none | yellow suspension | red ppt |
| 2-aminophenol | 0.59 | clear sol'n | red sol'n |
| 3-aminophenol | 0.59 | clear sol'n | amber sol'n |
| p-cresol | 0.594 | yellow suspension | red ppt |
| 2-aminobenzoic acid | 0.754 | clear sol'n | red sol'n |
| 3-aminobenzoic acid | 0.754 | clear sol'n | red sol'n |
| 4-aminobenzoic acid | 0.754 | clear sol'n | red sol'n |
| 4-aminobenzenesulfonic acid | 0.95 | clear sol'n | red sol'n |
| 4-amino-o-cresol | 0.68 | clear sol'n | red sol'n |
| carbohydrazide | 0.50 | clear sol'n | pale yellow sol'n |

EXAMPLE 4

The procedure described in Example 1 was modified by using 10 ml of diethanolamine instead of 10 ml of aqueous sodium hydroxide solution. This modified procedure was utilized to obtain the results enumerated in Table IV. These results illustrate that sodium sulfanilate prevents precipitation in a manner comparable to a conventional carbohydrazide treatment.

TABLE IV

Precipitation Test Results

| Amine | Amount (g) | Observations at 48 hours. |
|---|---|---|
| none | none | turbid, yellow gum ppt. |
| hydroxylamine sulfate | 0.451 | clear, pale yellow solution |
| carbohydrazide | 0.495 | clear, yellowish solution |
| sodium sulfanilate | 1.073 | clear, reddish yellow solution |

EXAMPLE 5

10 ml of a 10% aqueous sodium hydroxide solution was placed in a centrifuge tube. The amine to be tested was then added and mixed well. Next, 0.5 ml of vinyl acetate was added to the aqueous solution, followed by shaking of the solution for one minute. The solution was stored overnight at 110°–120° F. Observations were made after adding enough water to make up a total solution volume of 15 ml and mixing.

The results of Table V indicate the activity of the various compounds on an equivalent weight basis. Sodium sulfanilate showed no red precipitates at half equivalent weight per mole of acetaldehyde, while carbohydrazide and hydroxylme sulfate gave precipitates at this treatment rate.

TABLE V

Precipitation Test Results

| Amine | Amount (g) | Equivalents | Observations at 24 hrs. |
|---|---|---|---|
| none | none | none | red precipitate |
| hydroxylamine sulfate | 0.226 | 0.5 | red precipitate |
| hydroxylamine sulfate | 0.451 | 1 | pale yellow, slightly hazy solution |
| carbohydrazide | 0.124 | 0.5 | yellow precipitate |
| carbohydrazide | 0.248 | 1 | clear, colorless solution |
| carbohydrazide | 0.495 | 2 | clear, colorless solution |
| sodium sulfanilate | 0.504 | 0.5 | red clear solution |
| sodium sulfanilate | 1.073 | 1 | clear, dark red solution |

We claim:

1. A method of inhibiting the formation of fouling deposits occurring on the surfaces of an alkaline scrubber used to wash acid gases generated during the manufacture of olefins, which deposits are formed by base-catalyzed condensation reactions during the scrubbing of pyrolytically produced hydrocarbons contaminated with oxygen-containing compounds with an alkaline solution having a pH>7, which comprises adding-an effective deposit-inhibiting mount of an alkaline solution-soluble substituted aromatic amine selected from the group consisting of: 2-aminophenol, 4-aminophenol, 4-aminobenzenesulfonic acid and salts thereof, 4-amino-o-cresol, 3-aminophenol, 2-aminobenzoic acid and salts thereof, 3-aminobenzoic acid and salts thereof, and 4-aminobenzoic acid and salts thereof to the alkaline solution.

2. The method of claim 1 wherein the substituded aromatic amine is the sodium salt of 4-aminobenzenesulfonic acid.

3. The method of claim 1 wherein the substituted aromatic amine is recovered for re-use.

4. The method of claim 1 wherein the pyrolytically-produced hydrocarbon is ethylene.

5. The method of claim 1 wherein the oxygen-containing compound is a carbonyl compound.

6. The method of claim 5 wherein the carbonyl compound is acetaldehyde.

7. The method claim 1 wherein the hydrocarbons are produced by the pyrolytic cracking of hydrocarbon feedstocks.

8. The method of claim 7 wherein the hydrocarbon feedstocks are selected from the group consisting of ethane, propane, butane, naphtha and mixtures thereof.

9. The method of claim 8 wherein the hydrocarbon is in a gaseous phase.

10. The method of claim 5 wherein the substituted aromatic amine is added to the alkaline scrubber in an amount representing a molar ratio of amine to carbonyl from about 1.0:10.0 to about 1.0:25.0.

11. The method of claim 5 wherein the substituted aromatic amine is added to the alkaline scrubber in an amount representing a molar ratio of amine to carbonyl from about 1.0:3.0 to about 1.0:9.0.

12. The method of claim 5 wherein the substituted aromatic amine is added to the alkaline scrubber in an amount representing a molar ratio of amine to carbonyl from about 1.0:1.0 to about 1.0:2.0.

13. The method of claim 1 wherein the scrubber is a caustic scrubber.

14. The method of claim 1 wherein the scrubber is an amine scrubber.

* * * * *

UNITED STATES PATENT AND TRADEMARK OFFICE
CERTIFICATE OF CORRECTION

PATENT NO. : 5,714,055
DATED : February 3, 1998
INVENTOR(S) : Vincent E. Lewis & Natu R. Patel It is certified that error appears in the above-indentified patent and that said Letters Patent is hereby corrected as shown below:

Column 6, Claim 1, Line 49
"...effective deposit-inhibiting mount of..."

LETTERS PATENT SHOULD READ AS:

...effective deposit-inhibiting amount of...

Signed and Sealed this

Twenty-first Day of April, 1998

Attest:

BRUCE LEHMAN

Attesting Officer

Commissioner of Patents and Trademarks